United States Patent [19]

Kawase et al.

[11] Patent Number: 5,064,441
[45] Date of Patent: Nov. 12, 1991

[54] HAIR TREATMENT COMPOSITION, BLEACHING COMPOSITION AND HAIR COLOR TONE MODIFIER COMPOSITION

[75] Inventors: Jiro Kawase, Funabashi; Kazuo Ukaji, Chiba; Emi Nagashima, Ichikawa, all of Japan

[73] Assignee: Kao Corporation, Tokyo, Japan

[21] Appl. No.: 511,216

[22] Filed: Apr. 19, 1990

[30] Foreign Application Priority Data

Apr. 24, 1989 [JP] Japan .................................. 1-103977

[51] Int. Cl.⁵ .......................... A61K 7/13; D06L 3/02
[52] U.S. Cl. .......................................... 8/405; 8/111; 8/406
[58] Field of Search ............................ 8/111, 405, 406

[56] References Cited

U.S. PATENT DOCUMENTS

| | | | |
|---|---|---|---|
| 3,632,295 | 1/1972 | Hall et al. | 8/111 |
| 3,838,966 | 10/1974 | Barchas et al. | 8/405 |
| 4,302,199 | 11/1981 | Juneja | 8/405 |
| 4,609,475 | 9/1986 | Hanlon et al. | 252/8.553 |

FOREIGN PATENT DOCUMENTS

| | | |
|---|---|---|
| 0335477 | 1/1989 | European Pat. Off. |
| 0327345 | 2/1989 | European Pat. Off. |
| 2028818 | 6/1970 | Fed. Rep. of Germany |
| 3149978 | 12/1981 | Fed. Rep. of Germany |
| 61-55483 | 11/1986 | Japan |
| 62-37004 | 8/1987 | Japan |
| 2192645 | 7/1987 | United Kingdom |

OTHER PUBLICATIONS

European Search Report.

Primary Examiner—Paul Lieberman
Assistant Examiner—William S. Parks
Attorney, Agent, or Firm—Birch, Stewart, Kolasch & Birch

[57] ABSTRACT

The present invention provides the following hair-treatment composition, bleaching composition and hair color tone modifier composition:

a hair-treatment composition containing:
(1) a ferrous salt, and
(2) a nonreducing organic chelate-forming compound capable of forming a chelate compound together with a ferrous ion, and having a pH value of from 3 to 6, wherein the stability constant ($K_1$) between said ferrous ion and said nonreducing organic chelate-forming compound is lower than 3 and the ferrous salt, which is the chelate compound of said ferrous ion with said nonreducing organic chelate-forming compound, is highly soluble in water;

a hair-treatment composition containing:
(1) a ferrous salt, and
(2) a nonreducing organic chelate-forming compound represented by the following general formula (I):

$$R-COOH \atop | \atop (OH)_m \qquad (I)$$

wherein R represents a straight-chain or branched hydrocarbon group having 1 to 10 carbon atoms or an oxane ring, and m is an integer of from 1 to 6, capable of forming a chelate compound with a ferrous ion and having a pH value of from 3 to 6;

a bleaching composition consisting of either one of the above-mentioned hair-treatment compositions as the primary agent together with an aqueous composition containing 0.01 to 3% by weight of hydrogen peroxide and having a pH value of from 3 to 6 as the secondary agent; and a hair color tone modifier composition obtained by adding a direct dye to the primary and/or secondary agents of the above-mentioned bleaching composition.

4 Claims, 2 Drawing Sheets

HAIR TREATMENT COMPOSITION, BLEACHING COMPOSITION AND HAIR COLOR TONE MODIFIER COMPOSITION

BACKGROUND OF THE INVENTION

1. Field of the Invention

This invention relates to pretreatment agents to be used before bleaching or dyeing horny fibers such as the hair or idle hair, more particularly, a hair-treatment composition capable of supplying ferrous ions in a stable state to the horny fibers under weakly acidic mild conditions; a bleaching composition whereby the horny fibers such as the hair or idle hair can be bleached without giving much damage thereto under weakly acidic mild conditions while scarcely irritating, for example, the skin during the bleaching process; and a hair color tone modifier composition (hair dyeing composition) obtained by adding a hair dye to said bleaching composition.

2. Description of the Prior Art

Known bleaching agents for horny fibers such as the hair or idle hair contain hydrogen peroxide as an essential factor of their constituents. In most cases, this hydrogen peroxide, including perborates and percarbonates capable of liberating hydrogen peroxide at the application, would exert a bleaching effect in an aqueous state so as to oxidize and bleach melanin contained in the horny fibers such as the hair or idle hair. Such a bleaching agent is generally applied in the form of an alkaline aqueous solution (pH 8 to 11) in order to fully achieve the bleaching effect of the hydrogen peroxide. However there is a problem that hydrogen peroxide contained in an alkaline aqueous composition is unstable, which makes it difficult to store such a composition for a prolonged period of time.

Thus a bleaching agent containing hydrogen peroxide is frequently supplied in the form of a one-pack powdery bleaching agent, which is to be dissolved so as to give an alkaline aqueous solution at the application, or a two-pack bleaching agent) wherein a powdery or aqueous alkaline agent composition is to be mixed with a water-soluble hydrogen peroxide composition immediately before the application. In order to fully achieve the bleaching effect of these powdery one-pack and two-pack bleaching agents, it is required to elevate the pH value within an alkaline region or to increase the hydrogen peroxide content at the application. However these treatments, namely, the elevated pH value or increased hydrogen peroxide content would irritate the skin and mucosae so as to damage fibers including the hair.

Thus a pretreatment with ferrous ions has been conducted before bleaching or dyeing horny fibers such as the hair or idle hair in order to minimize the damage to the hair or improve the bleaching or dyeing effect.

For example, U.S. Pat. No. 3,632,295 discloses a two-stage method for bleaching the hair comprising applying the primary agent containing a ferrous salt to the hair and then applying an alkaline aqueous solution of hydrogen peroxide (of pH 8 to 11) to the hair as the secondary agent; Japanese Patent Publication No. 37004/1987 discloses a three-pack bleaching agent which consists of the primary agent containing a sulfite, the secondary agent containing a ferrous salt and the tertiary agent containing unstable hydrogen peroxide; and Japanese Patent Publication No. 55483/1986 discloses a two-pack hair dye consisting of the primary agent in the form of a commonly used hair tonic containing a ferrous salt and the secondary agent which is in the form of a hair conditioner containing a color former and may be used at an appropriate stage thereafter.

Furthermore, West German Patent No. 3,149,978 discloses a method comprising applying a ferrous compound as a reducing agent together with phosphorous acid to keratin fibers and then bleaching the keratin fibers with hydrogen peroxide.

An aqueous solution of a ferrous salt to be used as a pretreatment agent suffers from some troubles such that it would form hardly soluble ferrous hydroxide at a pH value of 5 or higher and that it would irritate the skin or mucosae at a pH value of 3.0 or lower. In order to stably and safely penetrate a ferrous salt into the hair, therefore, it has been attempted to control the pH value by using an ferrous salt solution as a buffer system. However there are still some problems in this method. Among organic acids commonly used in a buffer system, acetic acid has a characteristic odor while citric acid would cause the coloration of a chelate compound thereof with the ferrous ion.

When an alkaline aqueous solution of hydrogen peroxide is to be used as a bleaching agent, as in the case of the above-mentioned method of the U.S. Pat. No. 3,632,295, the hydrogen peroxide in said alkaline aqueous solution of hydrogen peroxide is unstable. Thus it is difficult to provide a stable aqueous composition available in practice unless the product is formulated into a three-pack composition wherein an alkali composition (the secondary agent) is mixed with a water-soluble hydrogen peroxide composition (the tertiary agent) immediately before the application.

On the other hand, the above-mentioned three-pack bleaching agent of the Japanese Patent Publication no. 37004/1987 cannot always be convenient, since it requires a complicated bleaching procedure and a long treatment period.

In the case of the above-mentioned bleaching method described in the West German Patent No. 3,149,978, furthermore, sufficient care should be taken in the pretreatment conducted under strongly acidic conditions and in the rinsing with an acidic solution such as phosphoric acid for removing the remaining phosphorous acid. Further, this product would sometimes cause significant irritation on the skin and mucosae when applied to the body.

When a hydrogen peroxide solution alone is to be used within a weakly acidic or neutral region, a satisfactory bleaching effect can be scarcely achieved. When the hydrogen peroxide concentration is increased or the solution is repeatedly used in order to enhance the bleaching effect, fibers including the hair would be frequently damaged.

SUMMARY OF THE INVENTION

It is a first object of the present invention to provide a hair-treatment composition stably containing ferrous ions which would scarcely irritate the skin or mucosae.

It is a second object of the present invention to provide an aqueous bleaching composition, which has high safety to the skin and mucosae, exerts a bleaching effect superior to those of known alkalihydrogen peroxide bleaching agents and can be easily handled, as well as a hair color tone modifier composition (hair dyeing composition) whereby the color tone of the hair can be modified.

The present inventors have conducted extensive studies and thus found a hair-treatment composition which can stabilize ferrous ions within a pH range safe to the skin and mucosae while scarcely damaging the hair. suppress the formation of hardly soluble ferrous hydroxide and effectively and rapidly penetrate the ferrous ions into the hair such a composition can achieve the first object of the present invention and can be obtained by adding a specific compound to a hair-treatment composition so as to form a chelate compound of said compound with ferrous ions.

The present inventors have further conducted studies on the convenience, storage stability and reduction of irritation of bleaching agents. As a result. they have found out that the second object of the present invention can be achieved by formulating a two-pack composition consisting of the above-mentioned hair-treatment composition as the primary agent and an aqueous composition. which contains hydrogen peroxide at a specific concentration and has a pH value adjusted within a specific range, as the secondary agent.

The present invention has been completed based on these findings. Accordingly, the invention provides for a hair-treatment composition comprising:
  (1) a ferrous salt, and
  (2) a nonreducing organic chelate-forming compound capable of forming a chelate compound with a ferrous ion,
and having a pH value of from 3 to 6, wherein the stability constant ($K_1$) between said ferrous ion and said nonreducing organic chelate-forming compound is lower than 3 and the ferrous salt, which is the chelate compound of said ferrous ion with said nonreducing organic chelate-forming compound, is highly soluble in water. This hair-treatment composition will be called the first hair-treatment composition hereinafter.

Furthermore, the present invention provides another hair-treatment composition comprising:
  (1) a ferrous salt, and
  (2) a nonreducing organic chelate-forming compound represented by the following general formula(I):

wherein R represents a straight chain or branched hydrocarbon group having 1 to 10 carbon atoms or an oxane ring, and
m is an integer of from 1 to 6,
capable of forming a chelate compound with a ferrous ion and having a pH value of from 3 to 6. This hair-treatment composition will be called the second hair-treatment composition hereinafter. In the above general formula (I), the hydroxyl group may be bound at any position to the hydrocarbon group R.

The present invention furthermore provides a bleaching composition which consists of the above-mentioned first or second hair-treatment composition as the primary agent and an aqueous composition containing 0.01 to 3% by weight of hydrogen peroxide and having a pH value of from 3 to 6 as the secondary agent.

The present invention furthermore provides a hair color tone modifier composition obtained by adding a direct dye to the above-mentioned primary agent and-/or the secondary agent of the above-mentioned bleaching composition.

The first and second hair-treatment compositions of the present invention, in which ferrous ions are stably blended. can supply the ferrous ions in a stable state to the horny fibers. Thus the hair can be excellently bleached or dyed without being damaged. Further these compositions are adjusted to a pH value of from 3 to 6 and thus scarcely irritate the skin or mucosae.

Further, the bleaching composition of the present invention is highly safe to the skin and mucosae and exerts a bleaching effect superior to those of known alkali-hydrogen peroxide bleaching agents. In addition, it can be readily handled while scarcely damaging the hair.

Furthermore, the hair color tone modifier composition of the present invention is highly safe to the skin and mucosae and can be easily handled so as to widely modify the color tone of the hair. [Function]

The first or second hair-treatment composition of the present invention may be used in the following manner. First, said composition is applied to horny fibers such as the hair and then slightly rinsed. Thus the ferrous salt is penetrated into the hair which prevents the hair from being damaged in the subsequent bleaching or dyeing step. In addition, the bleaching and dyeing can be excellently conducted.

The bleaching composition of the present invention may be used a follows. First, horny fibers such as the hair are treated with the primary agent and weakly rinsed. Next, the secondary agent is applied to the hair, which is allowed to dry as such or dried by heating with, for example, a blower. Thus the hair is bleached. Alternately, the secondary agent may be washed away after the completion of the bleaching. if desired.

The hair color tone modifier composition of the present invention may be used in the following manner. First, the hair is treated with the primary agent and weakly rinsed. Next, the secondary agent is applied as such to the hair. which is allowed to dry as such or dried by heating with, for example. a blower. Thus the color tone of the hair can be modified and dyeing can be excellently conducted.

DETAILED DESCRIPTION OF THE INVENTION

Figure 1:
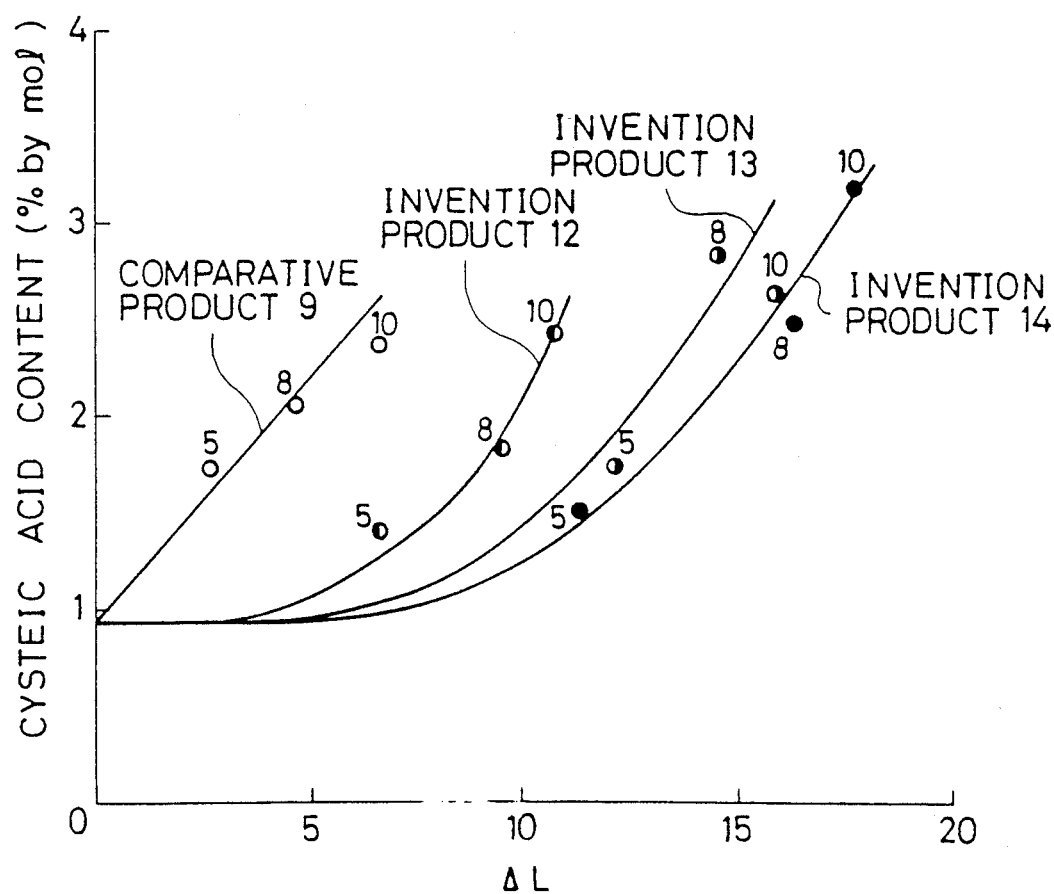
FIGS. 1 and 2 are each a graph showing a relationship between the lightening effect observed in the bleached hair and the content of cysteic acid.

The first hair-treatment composition of the present invention is an aqueous composition containing a ferrous salt and having a pH value adjusted to from 3 to 6.

Examples of the ferrous salt include ferrous acetate. ferrous nitrate, ferrous sulfate and ferrous chloride. Among these compounds, ferrous sulfate and ferrous chloride are preferable from the viewpoints of, for example, odor. The ferrous salt may be preferably contained in the first hair-treatment composition of the present invention in an amount of from 0.01 to 10% by weight.

When the pH value of said hair-treatment composition is adjusted within the range as specified above, said composition becomes safe to the skin and mucosae during treatment of the hair. Further, it scarcely damages fibers and the ferrous ions of the ferrous salt can be readily incorporated into the hair to form a complex with melanin. The pH value of the first hair-treatment composition of the present invention may be adjusted to from 3 to 6 by using a commonly employed acid such as hydrochloric or sulfuric acid or a common alkaline aqueous solution such as a sodium hydroxide or potassium hydroxide aqueous solution.

The first hair-treatment composition of the present invention further contains a nonreducing organic chelate-forming compound capable of forming a chelate compound with a ferrous ion. The stability constant [$K_1$; refer to Chaberek; "Organic Sequestering Agents", published by John Wiley (1959)] between said ferrous ion and said nonreducing organic chelate-forming compound should be lower than 3 and a ferrous salt, which is the chelate compound of the above-mentioned ferrous ion and the above-mentioned nonreducing organic chelate-forming compound, should be highly soluble in water. The expression "highly soluble in water" as used herein means that the solubility of said ferrous salt in purified water at 20° C. is 0.1% by weight or more.

When the stability constant ($K_1$) of the ferrous salt, namely, the above-mentioned chelate compound is adjusted to lower than 3, the ferrous salt can be more stably blended and stored in the form of an aqueous solution. The above-mentioned nonreducing organic chelate-forming compound is a compound which forms a chelate compound with a ferrous ion, suppresses the formation of a hydroxo complex of said ferrous ion, which is insoluble and forms a precipitate, and promotes the effective and rapid penetration of the ferrous ion into the hair. As the nonreducing organic chelate-forming compound, those represented by the following general formula (II) are preferable:

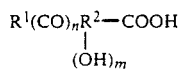

$$R^1(CO)_nR^2-COOH \atop (OH)_m \qquad (II)$$

In the above general formula (II), $R^1$ wherein $R^2$ may be either the same or different from each other and $R^1$ preferably represents a hydrogen atom, a straight-chain or branched alkyl group having one to five carbon atoms or an alkenyl group having one to five carbon atoms, $R^2$ wherein preferably represents a straight-chain or branched alkyl group having one to five carbon atoms or an alkenyl group having one to five carbon atoms, n is preferably from 0 to 2 and m is preferably from 0 to 6. Examples of such a nonreducing organic chelate-forming compound include organic acids such as lactic acid, glycolic acid, hydroxybutyric acid, glyceric acid, β-hydroxyglutaric acid, gluconic acid and glucuronic acid. By taking the odor into consideration, it is still preferable to use a hydroxy carboxylic acid such as lactic acid or glycolic acid. It is undesirable to use commonly employed organic chelate-forming compounds, for example, citric acid, or its salts, or ethylenediaminetetraacetic acid or its salts, since each of these compounds has a stability constant ($K_1$) with a ferrous ion exceeding 3 and the formation of a complex of said compound with a ferrous ion would lower the oxidation potential of the complex. When the composition thus obtained is stored, in particular at a high temperature, therefore, the complex would be partially oxidized by the contact thereof with the dissolved oxygen in the composition or with the atmosphere, which would frequently cause coloration and the formation of a $Fe^{3+}$ complex.

Furthermore, succinic acid, malic acid and tartaric acid would each form a complex salt with a ferrous ion. Although this complex salt has a stability constant ($K_1$) lower than 3, it has only a low solubility in water and thus can be hardly obtained in the form of a stable aqueous composition. Thus it is also undesirable to use there acids.

The above-mentioned nonreducing organic chelate-forming compound may be preferably contained in the first hair-treatment composition of the present invention in an amount of 0.1 to 10.0% by weight.

A nonreducing organic chelate-forming compound, which has a stability constant ($K_1$) lower than 3 and forms a chelate compound (i.e., a ferrous salt) highly soluble in water, can be used together with an organic reducing agent such as ascorbic acid.

Now the second hair-treatment composition of the present invention will be described in detail.

Similar to the above-mentioned first hair-treatment composition, the second hair-treatment composition of the present invention is an aqueous composition containing a ferrous salt and having a pH value adjusted to from 3 to 6.

As said ferrous salt, those described with respect to the above-mentioned first hair-treatment composition may be used. Similar to the case of the above-mentioned first hair-treatment composition, the ferrous salt may be preferably contained in the composition in an amount of from 0.01 to 10% by weight.

The pH value of the second hair-treatment composition of the present invention may be adjusted in the same manner as the one employed in the case of the above-mentioned first hair-treatment composition.

As the nonreducing organic chelate-forming compound of the above-mentioned general formula (I) to be used in the second hair-treatment composition of the present invention, lactic acid, glycolic acid, hydroxybutyric acid, glyceric acid, gluconic acid and glucuronic acid may be used. By taking the odor into consideration, it is still preferable to use lactic acid or glycolic acid. This nonreducing organic chelate-forming compound (I) may be preferably contained in the second hair-treatment composition of the present invention in an amount of from 0.1 to 10.0% by weight. The second hair-treatment composition of the present invention may further contain an organic reducing agent such as ascorbic acid as another chelate-forming compound.

It is preferable to add a cationic polymer and/or a cationic surfactant to the above-mentioned first and second hair-treatment compositions of the present invention to thereby improve the texture of the hair. In order to further improve this conditioning effect, these compositions may be formulated into an emulsion by optionally adding appropriate additive(s) such as a higher alcohol thereto.

Furthermore, the above-mentioned first and second hair-treatment compositions of the present invention may be processed into various forms, for example, rinse, treatment or preshampoo treatment. Thus various additives commonly used in the production of these products, for example, UV absorbers, cationic surfactants, nonionic surfactants, wetting agents, thickners such as water-soluble polymers, pearlescent pigments such as glycol esters, antidandruff agents, medical ingredients such as vitamins, preservatives such as paraben, hair-setting polymers such as acrylic acid resin solutions, various perfumes and colorants may be added thereto, so long as the effects of the present invention are not deteriorated thereby.

In order to maintain the first and second hair-treatment compositions of the present invention in a stable state for a prolonged period of time, it is preferable to shut off these compositions from contact with external air. Therefore they may be preferably filled in hermetically sealed containers such as a laminate tube or an aerosol container. Examples of these containers include a double-wall aerosol container of a piston can type filled with a liquefied gas, for example, carbon dioxide, nitrogen, nitrous oxide, Freon, LPG or a mixture thereof, a nonaerosol double-well container of a piston can type, a batting can and an Excel System (mfd. by Container Industries Inc.) where a container is directly pressurized with a rubber so as to extrude its contents, which are substitutes for the above-mentioned piston cans, a laminate tube made of a gas-impermeable material and a unit-dose package.

The first and second hair-treatment compositions of the present invention may be used in, for example, the following manner.

The first or second hair-treatment composition of the present invention is applied to the hair of the body to be treated allowed to stand for a while, and weakly rinsed. This procedure is repeated so as to penetrate the ferrous salt into the hair. This treatment enhances the bleaching effect and prevent the hair from being damaged in the subsequent bleaching step with the use of hydrogen peroxide. When the hair is subsequently dyed with a dye composition containing a colorant such as tannic acid or gallic acid, alternately, the color would be developed by the reaction with iron which has been penetrated by the pretreatment with the first or second hair-treatment composition of the present invention. Thus the hair can be excellently dyed.

Now the bleaching composition of the present invention will be described in detail.

The bleaching composition of the present invention consists of the above mentioned first or second hair-treatment composition as the primary agent together with an aqueous composition containing hydrogen peroxide as the secondary agent.

The above-mentioned secondary agent in the bleaching composition of the present invention is an aqueous composition which is employed as a bleaching agent after treating the hair with the above-mentioned primary agent. The secondary agent contains hydrogen peroxide at a concentration of from 0.01 to 3% by weight and has a pH value adjusted to from 3 to 6. When the hydrogen peroxide concentration exceeds 3%, the hair might be damaged. When the pH value falls within the range as specified above, the composition can exert an excellent bleaching effect while lowering the damage to the hair and the irritation on the skin and mucosae in the treatment with the secondary agent. The pH value of this secondary agent can be adjusted in the same manner as that employed in adjusting the pH value of the above-mentioned first or second hair-treatment composition, namely, the primary agent.

The secondary agent can further contain a chelating agent, for example, EDTA, an oxyquinoline salt or acetanilide so as to stabilize the hydrogen peroxide.

When this bleaching composition is to be applied to the hair, the above-mentioned secondary agent may contain a polymer stable in the hydrogen peroxide system, for example, a specific ester type polymer having the following structural formula as a styling agent.

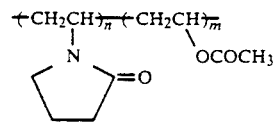

The above-mentioned ester polymer can impart a stable hair styling effect to the secondary agent containing hydrogen peroxide. Thus the secondary agent can be applied not only to a preparation to be used exclusively for bleaching but also to a commonly available hair styling agent which also exerts a bleaching effect and can be repeatedly used everyday, as will be shown hereinafter.

Thus the bleaching composition of the present invention, which scarcely damages horny fibers, can be widely used as, for example, a pretreatment agent to be used prior to bleaching or dyeing the fibers. Since it scarcely irritates the skin and mucosae, it is particularly suitable for treating idle hair and the hair.

Further, the primary agent of the bleaching composition of the present invention can be emulsified so as to give an aqueous gel, a cream or an emulsion. Furthermore, it can be formulated into a mousse by blending with a propellant. On the other hand, the secondary agent of the bleaching composition of the present invention may be used in the form of an aqueous liquid or a gel. Thus it can be applied to the hair as such. Alternately, it may be filled in a spray container or an aerosol container and sprayed at the time of use.

Now the hair color tone modifier composition (hair dyeing composition) of the present invention will be described in detail.

The hair color tone modifier composition of the present invention, which is obtained by applying the above-mentioned bleaching composition, is prepared by adding a direct dye to the above-mentioned primary and/or secondary agent of the bleaching composition. The addition of the dye to the primary and/or secondary agent of the bleaching composition makes it possible to bleach and lighten the inherent color of the hair as well as to dye the hair with the direct dye to thereby give a desired color during the bleaching stage. In addition, it is highly safe to the skin and mucosae and scarcely damages the hair. Therefore, the hair color tone modifier composition of the present invention can modify the color tone of the hair over a wide range of dark colors, including dark blond, dark brown and black, compared with a conventional hair color tone modifier composition which contains not an oxidation dye but a direct dye alone and exclusively depends on the dyeing effect of said dye.

Examples of the direct dye to be used in the hair color tone modifier composition of the present invention include basic direct dyes, acidic direct dyes, disperse dyes and nitro dyes. It is particularly preferable to use a basic dye such as an allyanol basic dye, a disperse dye, a nitro dye or a mixture thereof as the direct dye to be added to the secondary agent, since such a dye should be stable to the oxidizing agent.

When the above-mentioned direct dye is to be added to the primary agent of the bleaching composition alone, it may be preferably contained in the primary agent in an amount of from 0.0001 to 5% by weight. When it is to be added to the secondary agent of the bleaching composition alone, it may be preferably contained in the secondary agent in an amount of from 0.0001 to 5% by weight. When it is to be added to both of the primary and secondary agents, it may be preferably contained in the primary agent in an amount of from 0.0001 to 5% by weight and in the secondary agent in an amount of from 0.0001 to 5% by weight.

To further illustrate the present invention, and not by way of limitation, the following Examples will be given.

EXAMPLE 1: Stability test on hair-treatment composition

Hair-treatment compositions of formulations specified in the following Table 1 (invention products 1 and 2 and comparative products 1 to 7) were prepared. Then the stability of each product to a ferrous salt was tested. The stability was evaluated by determining the solubility of the ferrous salt when added to each product and observing the coloration of each product when stored at 40° C. for 20 days. Table 1 summarizes the results. When the ferrous salt is not dissolved but forms a precipitate upon addition, no coloration was examined any more.

TABLE 1

| Formulation (% by wt.) | Invention product 1 | Invention product 2 | Comparative product 1 | 2 | 3 | 4 | 5 | 6 | 7 |
|---|---|---|---|---|---|---|---|---|---|
| ferrous sulfate (7H$_2$O) | 0.98 | 0.98 | 0.98 | 0.98 | 0.98 | 0.98 | 0.98 | 0.98 | 0.98 |
| lactic acid | 4.5 | 4.5 | — | — | — | — | — | — | — |
| glycolic acid | — | 3.8 | — | — | — | — | — | — | — |
| ethylenediamine-tetraacetic acid | — | — | 1.46 | — | — | — | — | — | — |
| citric acid | — | — | — | 9.6 | — | — | — | — | — |
| succinic acid | — | — | — | — | 5.9 | — | — | — | — |
| tartaric acid | — | — | — | — | — | 7.5 | — | — | — |
| sodium bisulfite | — | — | — | — | — | — | 5.2 | — | — |
| phosphoric acid | — | — | — | — | — | — | — | 4.9 | — |
| ascorbic acid | 0.40 | 0.40 | 0.40 | 0.40 | 0.40 | 0.40 | 0.40 | 0.40 | 0.40 |
| sodium hydroxide | q.s. | q.s. | q.s. | q.s. | q.s. | q.s. | q.s. | q.s. | — |
| hydrochloric acid | — | — | — | — | — | — | — | — | q.s. |
| xanthan gum | 0.3 | 0.3 | 0.3 | 0.3 | 0.3 | 0.3 | 0.3 | 0.3 | 0.3 |
| purified water | balance | balance | balance | balance | balance | balance | balance | balance | balance |
| pH | 3.6 | 3.6 | 3.6 | 3.6 | 3.6 | 3.6 | 3.6 | 3.6 | 1.5 |
| Stability |  |  |  |  |  |  |  |  |  |
| coloration | no change | no change | change into orange or brown | browning | —* | —* | —* | —* | no change |
| solubility | soluble | soluble | soluble | soluble | precipitated | precipitated | precipitated | precipitated | soluble |

*Coloration was not tested since a precipitate was formed immediately after the addition.

As Table 1 shows, the ferrous salt was stably contained in each hair-treatment composition of the invention.

EXAMPLE 2: Skin irritation test of hair-treatment composition

The irritating effects on the skin of the invention products 1 and 2 and the comparative product 7, each obtained in Example 1, were evaluated in the following manner. A closed patch test was conducted with the use of Guinea pigs (N=4 or 5) for 24 hours. 48 hours thereafter, the conditions of the animals were observed with the naked eye and evaluated according to the following criteria. Table 2 gives the results.

Criteria:
0: no change,
1: slight erythema, and
2: significant erythema.

TABLE 2

| | Invention product 1 | Invention product 2 | Comparative product 7 |
|---|---|---|---|
| Skin irritation score | 0 | 0 | 1.0 |

As Table 2 shows, each invention product showed no skin irritation.

EXAMPLE 3: Application test of hair-treatment Composition

Hair-treatment compositions of the formulations specified in the following Table 3 (the invention products 3 to 5) were prepared.

TABLE 3

| Formulation (% by wt.) | Invention product 3 | 4 | 5 |
|---|---|---|---|
| ferrous sulfate (7H$_2$O) | 0.98 | 0.98 | 0.98 |
| ascorbic acid | 0.6 | 0.6 | 0.6 |
| lactic acid | 4.5 | 4.5 | 4.5 |
| cationized cellulose[1] | — | 0.5 | 0.5 |
| cationic surfactant[2] | 5.4 | 1.1 | — |
| cationic surfactant[3] | 2.0 | — | — |
| nonionic surfactant[4] | — | 0.5 | 0.5 |
| nonionic surfactant[5] | 1.0 | — | — |
| behenyl alcohol | 2.0 | — | — |
| propylene glycol | 10.0 | 4.0 | 4.0 |
| perfume | 0.2 | 0.2 | 0.2 |
| methylparaben | 0.3 | 0.3 | 0.3 |
| xanthan gum | 0.3 | 0.3 | 0.3 |
| sodium hydroxide | q.s. | q.s. | q.s. |
| purified water | balance | balance | balance |
| pH of composition | 3.8 | 3.8 | 3.8 |
| Form of composition | creamy | transparent | transparent |

Note:
[1] Polymer JR (mfd. by Union Carbide Corp.)
[2] Stearyltrimethylammonium chloride (30% aqueous solution).
[3] Dimethyldialkylammonium chloride [branched quaternary ammonium salt derived from commercially available oxo-synthesis alcohol having 12 to 15 carbon atoms (equivalent mixture of Dobanol 23 with Dobanol 25 mfd. by Mitsubishi Petrochemical Co., Ltd.), degreed of branching: 20%].
[4] Ethylene oxide adduct of a synthetic secondary alcohol having 11 to 15 carbon atoms (average number of added ethylene oxide molecules: ca. 9).
[5] Polyoxyethylene 2-octyldodecyl ether (average number of added etylene oxide molecules: ca. 20).

Further, a hair-dyeing cream of the following formulation was prepared.

| Formulation of hair-dyeing cream | | % by wt. |
| --- | --- | --- |
| (1) | self-emulsifiable glyceryl monostearate | 4.5 |
| (2) | ethylene glycol monostearate | 3.5 |
| (3) | polyoxyethylene sorbitan tristearate | 1.0 |
| (4) | paraffin wax | 3.0 |
| (5) | liquid paraffin | 25.0 |
| (6) | vaseline | 5.0 |
| (7) | ceresin wax | 2.0 |
| (8) | isopropyl myristate | 4.5 |
| (9) | sodium cetyl sulfate | 1.5 |
| (10) | gallic acid | 1.0 |
| (11) | ferrous sulfate | 1.0 |
| (12) | ascorbic acid | 0.2 |
| (13) | citric acid | 0.2 |
| (14) | ethylene carbonate | 10.0 |
| (15) | water | 37.1 |
| (16) | perfume | 0.5 |
| | total | 100.0 |

Preparation of Hair-dyeing Cream

The above-mentioned components (9), (10) and (13) were homogeneously dissolved in a portion of the purified water at approximately 80° C. The above components (1) to (8) were made molten by heating to approximately 90° C. and then added to the mixture solution obtained above under stirring. The resulting mixture was homogeneously stirred and cooled. The above-mentioned components (11) and (12) were homogeneously dissolved in the rest of the water and then added together with the component (14) to the mixture obtained above at 50° C. After mixing and cooling, the mixture was filled in an Excel bottle to thereby give a creamy hair-dye (hair-dyeing cream).

Dyeing

The effect of the invention product given in Table 3 was examined in the following manner. An appropriate amount of said invention product given in Table 3 (a conditioning composition) was applied to gray hair after shampooing and allowed to stand for several minutes. Then it was rinsed away and the hair was further treated with the above-mentioned hair-dyeing cream. This procedure was repeated. Thus, the white hair slowly turned black under very excellent conditions.

EXAMPLE 4: Application test of hair-treatment composition

A hair-dyeing lotion of the following formulation was prepared by the following method.

| Formulation | | % by wt. |
| --- | --- | --- |
| (1) | solid logwood extract (hematoxylin content: ca. 50%) | 2.0 |
| (2) | glucose | 1.0 |
| (3) | perfume | 0.5 |
| (4) | purified water | 96.5 |
| | total | 100.00 |

Preparation of Hair-dyeing Lotion

The above-mentioned component (1) was dissolved in component (4) under stirring. Next, components (2) and (3) were added thereto and stirring to thereby give a transparent aqueous solution (a hair-dyeing lotion).

Dyeing

Another effect of the product obtained in the above-mentioned Example 3 was examined in the following manner. An appropriate amount of the invention product given in Table 3 (conditioning composition) was applied to white hair after shampooing. Then it was allowed to stand for several minutes and rinsed away. Next, an appropriate amount of the above-mentioned hair-dyeing lotion was applied to the white hair. After being allowed to stand for several minutes, it was rinsed away. This procedure was repeated. Thus, the white hair slowly turned black under very excellent conditions.

EXAMPLE 5: Bleaching test of a bleaching composition

In this Example, invention products 6 to 11, each consisting of the primary and secondary agents listed in Table 4, were prepared and subjected to the following test.

Undamaged black hair of a German was used as the test hair. Samples each weighing 1 g were taken from the test hair and treated with each primary agent specified in Table 4 at 55° C. for 60 minutes. Next, the hair sample was washed with warm water for one minute and the excess moisture was removed. Then it was treated with the corresponding secondary agent specified in Table 4 at 55° C. for 60 minutes. The change in the color tone of the above-mentioned black hair thus treated with the primary and secondary agents was measured. The change in the color tone was determined by measuring the lightness (L) in the Hunter color difference meter and expressed by the change in the lightness ($\Delta L$) which is employed as a measure. Table 4 gives the results. The damage to the hair caused by the above-mentioned bleaching procedure was examined by using the content of cysteic acid formed by the treatment as a measure. Namely, the bleached hair was hydrolyzed and the content (% by mol) of the cysteic acid determined with an amino acid analyzer was compared. Table 4 gives the results.

The irritation on the skin was evaluated in the following manner. Each of the primary and secondary agents was subjected to a closed patch test for 24 hours with the use of Guinea gigs (N=4 or 5). 48 hours thereafter, the average scores were compared with each other.

−:0, ±:1, +:2, and ++:3.

In a comparative case, an aqueous solution of hydrogen peroxide was mixed with an alkali solution immediately before the use to thereby prepare the secondary agent (cf. Table 4), which was then applied to the hair so as to examine the effect of a conventional alkaline bleaching agent.

The results given in Table 4 suggest the following facts:
(1) The invention products 6 to 11 each showed a large change in L ($\Delta L$), which gave a remarkable lightening (bleaching) effect as compared with the comparative product 8.
(2) The invention products 6 to 11 each had a low cysteic acid content, when gave slight damage to the hair as compared with the comparative product 8. Furthermore, the invention products 6 to 11 each gave a slight irritating effect on the skin as compared with the comparative product 8.

TABLE 4

| Composition (%) | Invention product | | | | | | Comparative product 8 |
|---|---|---|---|---|---|---|---|
| | 6 | 7 | 8 | 9 | 10 | 11 | |
| Primary agent | | | | | | | |
| ferrous sulfate (7H$_2$O) | 0.98 | 0.98 | 0.98 | 0.98 | 0.98 | 0.98 | — |
| ascorbic acid | 0.6 | 0.6 | 0.6 | 0.6 | 0.6 | 0.6 | — |
| lactic acid | 4.5 | 4.5 | 4.5 | 4.5 | 4.5 | 4.5 | — |
| sodium hydroxide | q.s. | q.s. | q.s. | q.s. | q.s. | q.s. | — |
| xanthan gum | 0.3 | 0.3 | 0.3 | 0.3 | 0.3 | 0.3 | — |
| purified water | balance | balance | balance | balance | balance | balance | — |
| pH | 5.0 | 5.0 | 5.0 | 5.0 | 3.0 | 6.0 | — |
| Secondary agent | | | | | | | |
| hydrogen peroxide (30%) | 6.6 | 6.6 | 6.6 | 6.6 | 6.6 | 6.6 | 6.6 |
| acetic acid | 7.2 | 7.2 | 7.2 | 7.2 | 7.2 | 7.2 | — |
| acetanilide | 0.02 | 0.02 | 0.02 | 0.02 | 0.02 | 0.02 | 0.02 |
| oxyquinoline | 0.01 | 0.01 | 0.01 | 0.01 | 0.01 | 0.01 | 0.01 |
| sodium hydroxide | q.s. | q.s. | q.s. | q.s. | q.s. | q.s. | q.s. |
| aqueous ammonia (28%) | — | — | — | — | — | — | 3.1 |
| purified water | balance | balance | balance | balance | balance | balance | balance |
| pH | 3.0 | 4.0 | 5.0 | 6.0 | 4.0 | 4.0 | 10.4 |
| Lightening effect ($\Delta L$) | 15.8 | 14.3 | 15.1 | 16.8 | 13.8 | 12.1 | 7.3 |
| (hair color tone) | (dark blond) | (dark blond) | (dark blond) | (dark blond) | (dark blond) | (dark blond) | (dark brown) |
| Cysteic acid content (% by mol) | 1.11 | 1.33 | 0.89 | 1.12 | 1.25 | 1.67 | 2.1 |
| Skin irritation score | | | | | | | |
| Primary agent | 0 | 0 | 0 | 0 | 0.2 | 0 | — |
| Secondary agent | 1.4 | 1.25 | 1.0 | 1.0 | 1.25 | 1.25 | 2.6 |

EXAMPLE 6: Bleaching test of bleaching composition

In this Example, invention products 12 to 14 each consisting of the primary and secondary agents listed in the following Table 5 were prepared and subjected to the following bleaching test.

Similar to Example 5, samples, each weighing 1 g, of undamaged black hair of a German were prepared and treated with each primary agent listed in Table 5 at 55° C. for 60 minutes. Next, it was rinsed and the excess moisture was removed. Then the corresponding secondary agent listed in Table 5 was applied to the hair sample thus treated and dried by allowing it to stand overnight, as in the case of the application of a conventional set lotion. Subsequently, this treatment with the secondary agent was repeated everyday. Thus the treatment with the secondary agent was conducted ten times in total. In a comparative case, a hair sample was treated with the secondary agent of the comparative product 9 (listed in Table 5) in the same manner as the one described above. The results are given in Table 5 and FIG. 1.

The results given in Table 5 and FIG. 1 indicate that the invention products 12 to 14 each gave slight damage to the formation of cysteic acid, when compared with the comparative product 9 at the point providing for the same bleaching effect.

TABLE 5

| Composition (%) | Invention product | | | Comparative product 9 |
|---|---|---|---|---|
| | 12 | 13 | 14 | |
| Primary agent | | | | |
| ferrous sulfate (7H$_2$O) | 0.027 | 0.27 | 2.70 | — |
| ascorbic acid | 0.6 | 0.6 | 0.6 | — |
| lactic acid | 4.5 | 4.5 | 4.5 | — |
| sodium hydroxide | q.s. | q.s. | q.s. | — |
| xanthan gum | 0.3 | 0.3 | 0.3 | — |
| water | balance | balance | balance | — |
| pH | 3.6 | 3.6 | 3.6 | — |
| Secondary agent | | | | |
| hydrogen peroxide (30%) | 1.0 | 1.0 | 1.0 | 1.0 |
| acetic acid | 7.2 | 7.2 | 7.2 | 7.2 |
| acetanilide | 0.02 | 0.02 | 0.02 | 0.02 |
| oxyquinoline | 0.01 | 0.01 | 0.01 | 0.01 |
| sodium hydroxide | q.s. | q.s. | q.s. | q.s. |
| water | balance | balance | balance | balance |
| pH | 3.6 | 3.6 | 3.6 | 3.6 |
| Skin irritation score | | | | |
| Primary agent | 0.2 | 0 | 0 | — |
| Secondary agent | 0.2 | 0.2 | 0.2 | 0.2 |

EXAMPLE 7

In this Example, invention products 15 to 17 consisting of the primary and secondary agents listed in the following 6 were prepared and subjected to the following bleaching test.

Similar to Example 6, 1 g of undamaged black hair of a German was treated each with a primary agent listed in Table 6 at 35° C. for five minutes. Next, it was rinsed and the excess moisture was removed. Then the corresponding secondary agent listed in Table 6 was applied to the hair and dried by allowing it to stand overnight, as in the case of the application of a conventional set lotion. The procedure was repeated ten times in total everyday with the use of the primary agent together with the secondary agent. In the cases of the comparative products 10 to 12, the secondary agent listed in Table 6 was used alone in the treatment. Table 6 gives the results.

Figure 2:
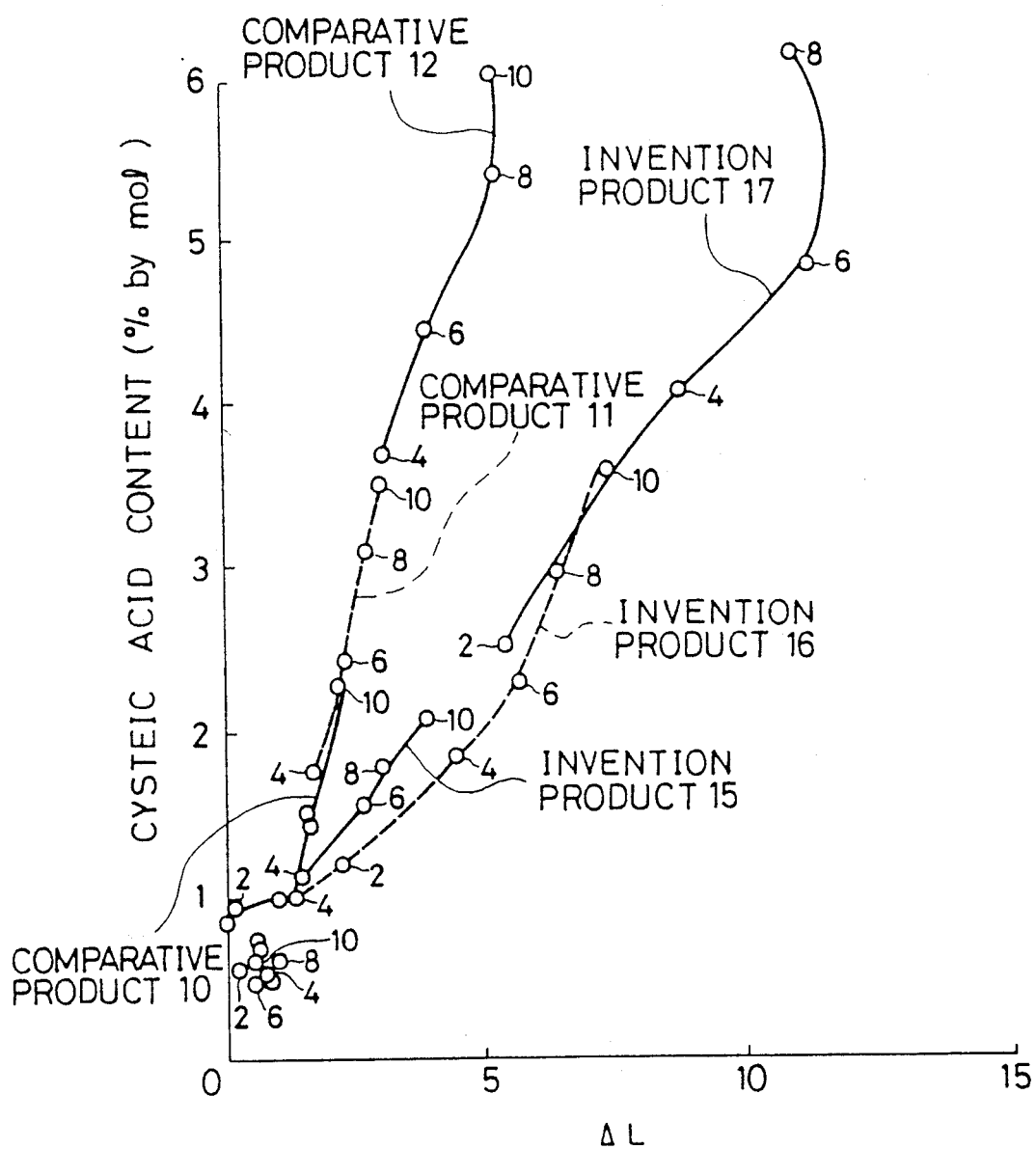

The results given in Table 6 and FIG. 2 indicate that the invention products 15 to 17 each gave slight damage to the hair, when compared with the comparative products 10 to 12 at the point providing for the same bleaching effect.

TABLE 6

| Composition (%) | Invention product | | | Comparative product | | |
| --- | --- | --- | --- | --- | --- | --- |
| | 15 | 16 | 17 | 10 | 11 | 12 |
| Primary agent | | | | | | |
| ferrous sulfate (7H$_2$O) | 0.98 | 0.98 | 0.98 | — | — | — |
| ascorbic acid | 0.6 | 0.6 | 0.6 | — | — | — |
| lactic acid | 4.5 | 4.5 | 4.5 | — | — | — |
| sodium hydroxide | q.s. | q.s. | q.s. | — | — | — |
| xanthan gum | 0.3 | 0.3 | 0.3 | — | — | — |
| purified water | balance | balance | balance | — | — | — |
| pH | 3.6 | 3.6 | 3.6 | — | — | — |
| Secondary agent | | | | | | |
| hydrogen peroxide (30%) | 1.7 | 3.3 | 9.9 | 1.7 | 3.3 | 9.9 |
| acetanilide | 0.02 | 0.02 | 0.02 | 0.02 | 0.02 | 0.02 |
| oxyquinoline | 0.01 | 0.01 | 0.01 | 0.01 | 0.01 | 0.01 |
| 75% phosphoric acid | q.s. | q.s. | q.s. | q.s. | q.s. | q.s. |
| purified water | balance | balance | balance | balance | balance | balance |
| pH | 3.6 | 3.6 | 3.6 | 3.6 | 3.6 | 3.6 |
| Skin irritation score | | | | | | |
| Primary agent | 0.2 | 0.2 | 0.2 | — | — | — |
| Secondary agent | 1.25 | 1.4 | 1.8 | 1.4 | 1.4 | 1.8 |

EXAMPLE 8: Conditioning effect of hair-treatment composition

In this Example, the conditioning effects of the invention products 3 to 5 obtained in Example 3 and a comparative product 13 of the formulation as specified in the following Table 7 were tested.

The invention products 3 to 5 and the comparative product 13 were applied to the hair. Then the touch of the hair at the application and that after drying were organoleptically evaluated to determine the conditioning effect of each product. Table 7 gives the results.

As Table 7 indicates, the invention products 3 to 5 showed each an excellent conditioning effect, while the comparative product 13 was inferior to them in conditioning effect.

TABLE 7

| | Invention product | | | Comparative product 13 |
| --- | --- | --- | --- | --- |
| | 3 | 4 | 5 | |
| Formulation (% by wt.) | | | | |
| ferrous sulfate (7H$_2$O) | 0.98 | 0.98 | 0.98 | 0.98 |
| ascorbic acid | 0.6 | 0.6 | 0.6 | 0.6 |
| lactic acid | 4.5 | 4.5 | 4.5 | 4.5 |
| cationized cellulose[1] | — | 0.5 | 0.5 | — |
| cationic surfactant[2] | 5.4 | 1.1 | — | — |
| cationic surfactant[3] | 2.0 | — | — | — |
| nonionic surfactant[4] | — | 0.5 | 0.5 | 0.5 |
| nonionic surfactant[5] | 1.0 | — | — | — |
| behenyl alcohol | 2.0 | — | — | — |
| propylene glycol | 10.0 | 4.0 | 4.0 | 4.0 |
| perfume | 0.2 | 0.2 | 0.2 | 0.2 |
| methylparaben | 0.3 | 0.3 | 0.3 | 0.3 |
| xanthan gum | 0.3 | 0.3 | 0.3 | 0.3 |
| sodium hydroxide | q.s. | q.s. | q.s. | q.s. |
| purified water | balance | balance | balance | balance |
| pH of composition | 3.8 | 3.8 | 3.8 | 3.8 |
| Form of composition | creamy | transparent | transparent | — |
| Conditioning effect | ⊚ | ⊚ | ⊚ | x |

Note: [1] to [5] are as defined above in Table 3.

EXAMPLE 9: Hair color tone modifier composition

In this Example, invention products 18 and 19 of the formulations specified in the following Table 8 were prepared. The invention product 18, wherein a direct dye was directly added to the primary agent, was suitable for daily use. The invention product 19, wherein a direct dye was directly added to the secondary agent, was a set lotion having a hair color tone modifying effect. The color tone of the hair could be excellently modified by using either of these compositions.

The first agents of the invention products 18 and 19 were each hermetically sealed in an Excel bottle.

TABLE 8

| Formulation (% by weight) | Invention product 18 | Invention product 19 |
| --- | --- | --- |
| Primary agent | | |
| ferrous sulfate (7H$_2$O) | 0.98 | 0.98 |
| ascorbic acid | 0.6 | 0.6 |
| lactic acid | 4.5 | 4.5 |
| silicone[1] | 0.5 | 0.5 |
| methylparaben | 0.3 | 0.3 |
| cationic surfactant[2] | 2.0 | 2.0 |
| cationic surfactant[3] | 5.5 | 5.5 |
| nonionic surfactant[4] | 1.0 | 1.0 |
| behenyl alcohol | 2.0 | 2.0 |
| propylene glycol | 10.0 | 10.0 |
| common salt | — | 1.0 |
| perfume | 0.2 | 0.2 |
| xanthan gum | 0.4 | 0.4 |
| sodium hydroxide | q.s. | q.s. |
| Dye | | |
| Sienna Brown[5] | 0.015 | — |
| Straw Yellow[5] | 0.005 | — |
| Madder Red[5] | 0.040 | — |
| disperse Violet[6] | 0.010 | — |
| HC blue No. 2[6] | 0.010 | — |

TABLE 8-continued

| Formulation (% by weight) | Invention product 18 | Invention product 19 |
|---|---|---|
| water | balance | balance |
| pH | 3.8 | 3.8 |
| Secondary agent | | |
| hydrogen peroxide (30%) | 1.8 | 1.8 |
| acetanilide | 0.02 | 0.02 |
| oxyquinoline | 0.01 | 0.01 |
| styling polymer*7 | 2.0 | 2.0 |
| phosphoric acid | q.s. | q.s. |
| Dye | | |
| Sienna Brown*5 | 0.005 | — |
| Straw Yellow*5 | — | 0.002 |
| Madder Red*5 | — | 0.0005 |
| water | balance | balance |
| pH | 3.0 | 3.0 |

Note:
*1 KF96 (mfd. by Toray Silicone Co.).
*2 Stearyltrimethylammonium chloride.
*3 The same as the one shown by *3 in Table 5 (Example 5).
*4 The same as the one shown by *4 in Table 5 (Example 5).
*5 Basic dye (mfd. by William, England).
*6 Nitro dye (described in CTFA Dictionary, U.S.A.).
*7 Luviskol K30 (mfd. by BASF).

What is claimed is:

1. A hair color tone modifier composition comprising:
   (1) a first hair treatment composition comprised of:
   (a) a ferrous salt, and
   (b) a non-reducing organic chelate-forming compound having the formula (II):

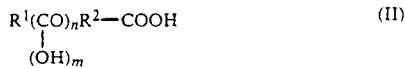

$$R^1(CO)_nR^2\text{—COOH} \quad\quad (II)$$
$$|$$
$$(OH)_m$$

wherein R and R may be the same of different and wherein R represents a hydrogen atom, a straight-chain or branched alkyl group having one to five carbon atoms or an alkenyl group having one to five carbon atoms, and wherein R represents a straight-chain or branched alkyl group having one to five carbon atoms or an alkenyl group having one to five carbon atoms, n is from 0 to 2 and m is from 0 to 6, and wherein when m is 1 to 6, said hydroxyl group may be bound at any position on said R; and wherein said non-reducing organic chelate-forming compound (II) is capable of forming a chelate compound with a ferrous ion having a pH of from 3 to 6, wherein the stability constant ($K_1$) between said ferrous ion and said non-reducing organic chelate-forming compound is lower than 3 and wherein said ferrous salt, which is the chelate compound, is highly soluble in water; and (2) a second aqueous composition containing 0.01 to 3% by weight of hydrogen peroxide having a pH from 3 to 6, wherein a direct dye is added to either composition (1) or (2).

2. A hair color tone modifier composition comprising:
   (1) a first hair treatment composition as claimed in claim 6; and
   (2) a second aqueous composition containing 0.01 to 3% by weight of hydrogen peroxide having a pH of from 3 to 6, and wherein 0.0001 to 5.0% of a direct dye is added to either composition (1) or (2).

3. A method for bleaching hair which comprises the sequential steps of:
   (a) applying to the hair a hair treatment composition as claimed in claim 5; and
   (b) applying to the hair at pH 3 to 6 and aqueous composition containing 0.01 to 3% by weight of hydrogen peroxide having a pH of from 3 to 6.

4. A method for bleaching hair which comprises the sequential steps of:
   (a) applying to the hair a hair treatment composition as claimed in claim 6 as the primary agent; and
   (b) applying to the hair at pH 3 to 6 an aqueous composition containing 0.01 to 3% by weight of hydrogen peroxide having a pH of from 3 to 6.

* * * * *